United States Patent [19]

Grigg et al.

[11] 4,180,576
[45] Dec. 25, 1979

[54] PURINES USEFUL FOR THE POTENTIATION OF ANTIBIOTICS

[75] Inventors: Geoffrey W. Grigg, Sydney; Desmond J. Brown, Canberra, both of Australia

[73] Assignee: Commonwealth Scientific Industrial Research Organization, Sydney, Australia

[21] Appl. No.: 828,875

[22] Filed: Aug. 29, 1977

Related U.S. Application Data

[63] Continuation-in-part of Ser. No. 613,879, Sep. 16, 1975, abandoned.

[51] Int. Cl.² .................. A61K 31/505; A61K 31/52; C07D 473/36
[52] U.S. Cl. .................................. 424/251; 424/253; 544/265; 260/243.3
[58] Field of Search .................. 424/253, 251; 260/252

[56] References Cited

U.S. PATENT DOCUMENTS

| 3,567,705 | 3/1971 | Cervy et al. | 260/112.5 |
| 3,929,993 | 12/1975 | Takita et al. | 424/177 |

OTHER PUBLICATIONS

Chemical Abstracts 75:106530m, 1971.

*Primary Examiner*—Leonard Schenkman
*Attorney, Agent, or Firm*—Christie, Parker & Hale

[57] ABSTRACT

Purines useful for the potentiation of antibiotics, particularly phleomycin and bleomycin, have the general formula:

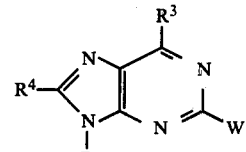

I or

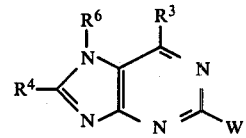

II wherein

W is selected from the group consisting of —SRCONR¹R², —SRCN, and —SRCOR¹, in which R is a —(CH$_2$)$_n$— group (n is an integer of 1 to 5) which may bear one or more side chain alkyl groups each having from 1 to 5 carbon atoms, and R¹ and R², which may be the same or different, are selected from hydrogen atoms and straight or branched chain alkyl groups having from 1 to 5 carbon atoms, or alternatively, R¹ and R² together comprise a polymethylene, oxapolymethylene or thiapolymethylene chain containing from 4 to 10 carbon atoms;

R³, R⁴, R⁵ and R⁶, which may be the same or different, are selected from hydrogen atoms and straight or branched chain alkyl groups having from 1 to 5 carbon atoms; and R, R¹, R², R³, R⁴, R⁵ and R⁶ may be substituted by one or more non-toxic substituents.

13 Claims, No Drawings

PURINES USEFUL FOR THE POTENTIATION OF ANTIBIOTICS

CROSS REFERENCE TO RELATED APPLICATION

This is a continuation-in-part of our Application Ser. No. 613,879 filed Sept. 16, 1975 now abandoned.

BACKGROUND OF THE INVENTION

This invention relates to purines useful for the potentiation of antibiotics, particularly phleomycin and bleomycin.

The preparation and structure of phleomycin and bleomycin is described in the following references:

(i) K. Maeda, H. Kosaka, K. Yagishita, H. Umezawa. J. Antibiot. (Tokyo) 9: 82–5 (1956). "A new antibiotic, phleomycin."
(ii) T. Takita. J. Antibiot. (Tokyo) 12: 285–9 (1959). "Studies on purification and properties of phleomycin."
(iii) T. Ikakawa, F. Iwami, H. Hiranaka, H. Umezawa. J. Antibiot. (Tokyo) 17: 194–9 (1964). "Separation of phleomycin components and their properties."
(iv) H. Umezawa, K. Maeda, T. Takeuchi, Y. Omaki. J. Antibiot. (Tokyo) 19: 200–9 (1966) "New Antibiotics, Bleomycin A & B."
(v) H. Umezawa, Y. Suhara, T. Takita, K. Maeda. J. Antibiot. (Tokyo) 19: 210–15 (1966). "Purification of Bleomycins."
(vi) T. Takita, Y. Muraoka, A. Fujii, H. Itoh, K. Maeda, H. Umezawa. J. Antibiot. (Tokyo) 25: 197–9 (1972). "The structure of the sulfur-containing chromophore of phleomycin, and chemical transformation of phleomycin to bleomycin."
(vii) T. Takita, Y. Muraoka, T. Yoshioka. J. Antibiot. (Tokyo) 25: 755–7 (1972). "The Chemistry of Bleomycin IX. The Structures of bleomycin and phleomycin."
(viii) H. Umezawa. Biomedicine. 18: 459–475 (1973). "Studies on Bleomycin: Chemistry and the Biological Action."

For the purposes of this invention, it is to be understood that references herein to phleomycin apply equally to bleomycin.

Phleomycin is a natural product with a wide range of antibiotic and antitumour activity, but has aroused little interest as a therapeutic agent because of its potential toxicity at effective dosage levels. With a view to taking advantage of the activity of phleomycin, attention has been given to the use of amplifying agents such as caffeine, which might offer a means of reducing phleomycin dosage levels while maintaining high therapeutic effectiveness. Caffeine itself shows nephrotoxicity, and many other amplifying agents which potentiate phleomycin to a high degree are similarly unsuitable either because they are themselves toxic or because they are metabolised in the body before reaching sites where their influence on phleomycin might be useful.

Typical of prior amplifying agents are a number of purine derivatives, particularly derivatives where an alkyl group is present on the $C_6$, $C_8$ atom or an imidazole nitrogen atom of the purine skeleton:

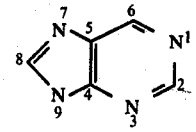

The toxicity of these prior amplifying agents is found to be reduced by the inclusion of an alkylthio group at the $C_2$ position but unfortunately the modification does not at the same time reduce their susceptibility to metabolic degradation. The basis of the present invention is the surprising discovery that the problem of metabolic degradation can be overcome by replacing the 2-alkylthio group with a C-substituted-alkylthio group, particularly a 2-carbamoylalkylthio, a 2-cyanoalkylthio or a 2-acylalkylthio group.

SUMMARY OF THE INVENTION

The present invention provides a compound of the general formula:

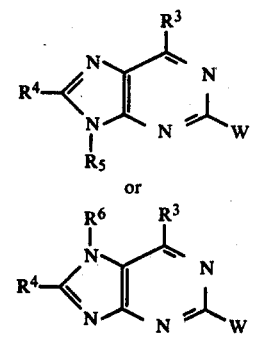

wherein: W is selected from the group consisting of $-SRCONR^1R^2$, $-SRCN$, and $-SRCOR^1$; in which R is selected from the group consisting of $-(CH_2)_n-$, wherein n is an integer from 1 to 5, $-(CH_2)_n-$, wherein n is an integer from 1 to 5 and which is substituted by at least one non-toxic substituent, $-(CH_2)_n-$, wherein n is an integer from 1 to 5, and which bears at least one alkyl group containing from 1 to 5 carbon atoms, and $-(CH_2)_n-$, wherein n is an integer from 1 to 5, and which bears at least one alkyl group containing from 1 to 5 carbon atoms and is substituted by at least one non-toxic substituent; wherein $R^1$ and $R^2$ are the same or different, and selected from the group consisting of hydrogen, a straight chain alkyl group containing from 1 to 5 carbon atoms, a straight chain alkyl group containing from 1 to 5 carbon atoms substituted by at least one non-toxic substituent, a branched chain alkyl group containing from 1 to 5 carbon atoms, and a branched chain alkyl group containing from 1 to 5 carbon atoms substituted by at least one non-toxic substituent, or wherein $R^1$ and $R^2$ together comprise a group selected from a polymethylene chain containing from 4 to 10 carbon atoms, a polymethylene chain containing from 4 to 10 carbon atoms substituted by at least one non-toxic substituent, an oxapolymethylene chain containing from 4 to 10 carbon atoms, an oxapolymethylene chain containing from 4 to 10 carbon atoms substituted by at least one non-toxic substituent, a thiapolymethylene chain containing from 4 to 10 carbon atoms, and a thiapolymethylene chain containing from 4 to 10 carbon atoms substituted by at least one non-toxic substituent;

and wherein $R^3$, $R^4$, $R^5$ and $R^6$, are the same or different, and selected from the group consisting of a hydrogen, a straight chain alkyl group containing from 1 to 5 carbon atoms, a straight chain alkyl group containing from 1 to 5 carbon atoms which is substituted by at least one non-toxic substituent, a branched chain alkyl group containing from 1 to 5 carbon atoms; and a branched chain alkyl group containing from 1 to 5 carbon atoms which is substituted by at least one non-toxic substituent; or a non-toxic salt thereof.

Each non-toxic substituent is preferably selected from the group consisting of fluoro, chloro, bromo, iodo, an alkoxy group, a thio analogue of an alkoxy group, a hydroxyl group, a thio analogue of a hydroxyl group, and an unsubstituted amino group; or from the group consisting of a carbamoyl group, a thio analogue of a carbamoyl group, an ester group, a thio analogue of an ester group and a substituted amino group. Within the latter group, each non-toxic substituent is preferably selected from the group consisting of $-CXNR_1R_2$, $-COXR_3$ or $-NR_4R_5$; in which X is selected from the group consisting of O or S, $R_1$, $R_2$ and $R_4$ are each selected from the group consisting of hydrogen and an alkyl group containing from 1 to 5 carbon atoms, and $R_3$ and $R_5$ are each an alkyl group containing from 1 to 5 carbon atoms.

Preferred compounds of this invention are compounds of the formulae:

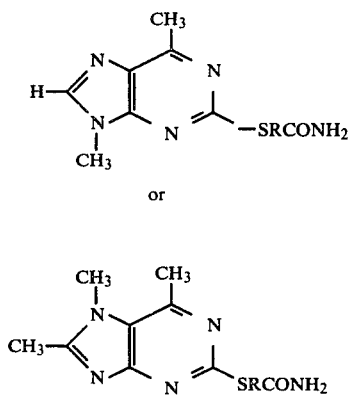

or

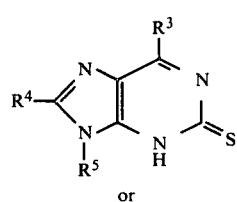

wherein R is as defined above.

Particularly preferred are the compounds 2-carbamoylmethylthio-6,9-dimethyl purine and 2-carbamoylmethylthio-6,8,9-trimethylpurine.

DESCRIPTION

Compounds of the above formulae I and II may be prepared by reaction of a thione of formula;

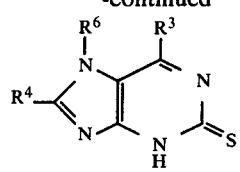

or

-continued

wherein $R^3$, $R^4$, $R^5$ and $R^6$ are as defined above with a haloalkylamide of formula:

$$X-R-CO-NR^1R^2 \qquad V$$

or with a haloalkylnitrile of formula:

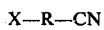

or with a haloalkylketone of formula:

wherein X is a halo substituent preferably a chloro substituent; and

R, $R^1$ and $R^2$ are as defined above.

Preferably the reaction is carried out by warming the reactants in mildly alkaline aqueous solution.

As described above, compounds of the formulae I or II above display antibiotic amplifying effect, and the present invention thus extends to compositions containing these compounds.

In combination with phleomycin, the compounds of this invention provide useful compositions for the treatment of various pathological conditions in human beings and domestic animals. Thus, phleomycin is notable for its antibiotic activity towards the bacterium *Eschericia coli* B, and is strongly taken up by cellular species at many sites in the body. With the alleviation of the toxicity problem permitted by the purine amplifiers of the present invention, phleomycin can now be a valuable agent for the treatment of *E. Coli* B infection at internal sites, such as the genito-urinary tract. In this respect the purine amplifiers of the present invention are particularly suited to assist in the selective treatment of bladder infections, since although the compounds can bind to cells, on the whole they are rapidly eliminated through the kidney to the bladder.

In the formulation of compositions, the relative proportions of antibiotic and purine amplifier will be a matter of choice according to the degree of potentiation desired. For most purposes, however, about $10^{-3}$ to $10^{-6}$ M concentration of phleomycin, and $2 \times 10^{-3}$ M to $4 \times 10^{-3}$ M concentration of the purine amplifier will be found to give satisfactory results. On occasion the most appropriate treatment regime might involve delaying administration of the amplifier in order to allow time for the antibiotic to become established at the infected site.

Thus, the present invention includes within its scope an amplifying pharmaceutical composition useful with antibiotics in the treatment of pathological conditions comprising an amplifying amount of a compound of the general formula I or II, or a non toxic salt thereof, in combination with a pharmaceutically acceptable adjuvant, carrier or diluent. The compositions may further comprise an effective amount of an antibiotic selected from the group consisting of phleomycin, bleomycin and mixtures thereof. In practice the compounds or compositions of the present invention may be administered orally, parenterally or topically.

The term "pharmaceutical composition" as used in the present specification, is meant to include compositions suitable for administration to domestic animals as well as compositions suitable for administration to human beings.

Solid compositions for oral administration include compressed tablets, pills, dispersible powders, and granules. In such solid compositions one or more of the compounds of the invention is, or are, admixed with at least one inert diluent such as calcium carbonate, potato starch, alginic acid, or lactose. The compositions may also comprise, as is normal practice, additional substances other than diluents, e.g. lubricating agents, such as magnesium stearate. Liquid compositions for oral administration include pharmaceutically acceptable emulsions, solutions, suspensions, syrups and elixers containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention for oral administration also include capsules of absorbable material such as gelatine containing one or more of the active substances with or without the addition of diluents or excipients.

Preparations according to the invention suitable for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

For topical or local administration, the compositions may be made up in the form of creams, solutions, gels or other ointments containing inert carriers and diluents commonly used in the art.

Finally, the present invention extends to a method of treatment of bacterial infections in an animal which comprises administering to the animal an effective amount of a compound selected from the group consisting of phleomycin, bleomycin, and mixtures thereof, prior to, simultaneous with or following administration of an amplifying amount of a compound of the general formula I or II, or a non-toxic salt thereof.

The invention will now be illustrated with reference to the following examples.

EXAMPLE I

2-Carbamoylmethylthio-6,9-dimethylpurine 6,9-Dimethylpurine-2-(3H)-thione (0.45 g), chloroacetamide (0.3 g), sodium hydrogen carbonate (0.25 g), and water (10 ml) were heated under reflux for 1 hr. Refrigeration gave a solid which recrystallised from water to give the carbamoylmethylthiopurine (0.40 g), m.p. 163°–164° (Found: C, 45.3; H, 4.9; N, 29.2. $C_9H_{11}N_5OS$ requires C, 45.6; H, 4.7; N, 29.5%).

EXAMPLE 2

2-Carbamoyl ($^{14}C$) methylthio-6,9-dimethylpurine (a) ($\alpha$-$^{14}C$)Chloroacetic acid (250 μCi) was transferred from a vial to a 2 ml distilling flask with the aid of anhydrous dichloromethane which was subsequently removed at −40°. Chloroacetic acid (116 mg) and benzoyl chloride (340 mg) were added to the flask which was then heated with a free bunsen flame to distil out chloroacetyl chloride (84 mg). The acid chloride was diluted with anhydrous acetone (2.0 ml) and shaken with anhydrous ammonium acetate (84 mg) for 20 min. The reaction mixture was filtered and the solid was washed with acetone. Evaporation of the filtrate and washing gave crude labelled chloroacetamide (70 mg).

(b) Labelled chloroacetamide (70 mg) prepared in para (a) above, 6,9-dimethylpurine-2-thione (102 mg), sodium hydrogen carbonate (57 mg), and water (2 ml) were heated under reflux for 45 min. Chilling gave the labelled carbamoylmethylthio-purine (83%): radioactivity was confined to the single t.l.c. spot which corresponded in appearance and position that of unlabelled material.

EXAMPLE 3

2-Carbamoylmethylthio-6,8,9-trimethylpurine

A mixture of chloroacetamide (102 mg), 6,8,9-trimethylpurine-2-thione (194 mg), and sodium hydrogen carbonate (100 mg) in 4 ml water was heated under reflux for 30 minutes and then chilled to give the carbamoylmethylthiopurine. A further crop of product was obtained on evaporation of the mother liquor. Yield 245 mg, m.p. 212°–213° (methanol) (Found: C, 47.5; H, 5.2; N, 27.8. $C_{10}H_{13}N_5OS$ requires C, 47.8; H, 5.2; N, 27.9), M+251, $\nu$ max 1675 cm$^{-1}$ (CO).

EXAMPLE 4

2-Carbamoylmethylthio($\alpha$-$^{14}C$)-6,8,9-trimethylpurine

A mixture of chloroacetamide ($\alpha$-$^{14}C$) (42 mg), 6,8,9-trimethylpurine-2-thione (78 mg), and sodium hydrogen carbonate (42 mg) in 2 ml water was treated as in Example 3 above to give 98 mg of the labelled carbamoylmethylthiopurine (0.49 $\nu$ Ci/mg) which showed only one spot under u.v. light when subjected to t.l.c. on alumina ($CHCl_3$:EtOH::10:1) and on silica ($CHCl_3$:EtOH::4:1). The single spot accounted for greater than 97% of total activity on the plate.

EXAMPLE 5

Metabolism of 2-Carbamoylmethylthio-6,9-dimethylpurine

An aqueous 2% solution of 2-carbamoyl($^{14}C$)methylthio-6,9-dimethylpurine (ca 0.5% labelled) was administered orally to 4 mice (0.1 ml each). After 90 hr, the collected urine contained 71% of the original radioactivity. The residue from evaporation was extracted with methanol. Preliminary t.l.c. of the extract indicated 2 major spots, each containing ca 40% of the radioactivity, the remaining 20% was located at the origin. The whole procedure was repeated with the unlabelled carbamoylmethylthiopurine using 15 mice, each dosed thrice with 0.2 ml at 24 hr intervals. The combined methanolic extracts were submitted to preparative t.l.c. on 2 mm silica plates. Elution of one zone gave unchanged 2-carbamoylmethylthio-6,9-dimethylpurine (from methanolether), identified by mixed m.p.

(163°), and comparative i.r. and mass spectra. The second zone gave 2-carbamoylmethylthio-6,9-dimethylpurin-8-one (from methanol-ether), m.p. 275°–277° (decomp.) identified with authentic material by similar criteria.

EXAMPLE 6

Measurement of biological activity

E. coli B was grown overnight to stationary phase in a glucose+salts medium (GT). An aliquot of washed cells was suspended in fresh GT containing phleomycin (1–2 μg/ml; dissolved immediately before the experiment) and incubated at 37° for 30 min. The cells were membrane filtered (0.45 μm) and resuspended in GT containing the purine under test (8 or 2 mM, according to solubility). Samples were removed at the outset and at intervals during 120 min. for estimation of the number of viable cells present using a commercial broth agar, Oxoid Blood agar base, for counts. In each series of assays, 8 mM caffeine was included as a standard.

The amplifying activity of each purine is expressed below as an adjusted activity relative to the mean activity of 8 mM caffeine set at 30 and hence independent of variations in conditions or in the amount of intrinsic activity of the phleomycin. Thus $A_m = N_O/N_{120}$ and $A_{ad} = 30 A_m/A_{caf}$ where $A_m$ is the measured activity of the purine, $A_{ad}$ is the adjusted activity, $N_O$ and $N_{120}$ are the numbers of viable cells at the beginning and after 120 min. respectively, and $A_{caf}$ is the measured activity of 8 mM caffeine.

| Compound | Activity* |
| --- | --- |
| 2—SCH$_2$CONH$_2$—6,9—Me$_2$ | 510 |
| 2—SCH$_2$CONH$_2$—6,8,9—Me$_3$ | 450 |

*very highly active - >10 × activity of caffeine at the same concentration (caffeine has an activity of 30 measured in this matter).

What is claimed is:
1. A compound of the general formula:

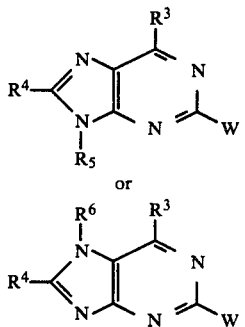

wherein: W is selected from the group consisting of —SRCONR$^1$R$^2$, —SRCN, and —SRCOR$^1$; in which R is selected from the group consisting of —(CH$_2$)$_n$—, wherein n is an integer from 1 to 5, having at least one side chain alkyl group containing from 1 to 5 carbon atoms; wherein R$^1$ and R$^2$ are the same or different, and selected from the group consisting of hydrogen, a straight chain alkyl group containing from 1 to 5 carbon atoms, and a branched chain alkyl group containing from 1 to 5 carbon atoms; and wherein R$^3$, R$^4$, R$^5$ and R$^6$, are the same or different, and selected from groups consisting of a hydrogen, a straight chain alkyl group containing from 1 to 5 carbon atoms and a branched chain alkyl group containing from 1 to 5 carbon atoms; or a non-toxic salt thereof.

2. A compound of the general formula:

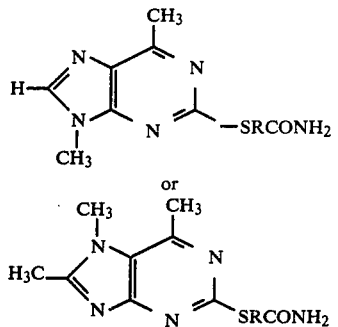

wherein R is selected from the group consisting of —(CH$_2$)$_n$—, wherein n is an integer from 1 to 5, and —(CH$_2$)$_n$—, wherein n is an integer from 1 to 5, having at least one side chain alkyl group containing from 1 to 5 carbon atoms; or a non-toxic salt thereof.

3. 2-carbamoylmethylthio-6,9-dimethyl purine.
4. 2-carbamoylmethylthio-6,8,9-trimethyl purine.
5. An amplifying pharmaceutical composition useful with antibiotics in the treatment of tumors and bacterial infections comprising an amplifying amount of a compound having the formula:

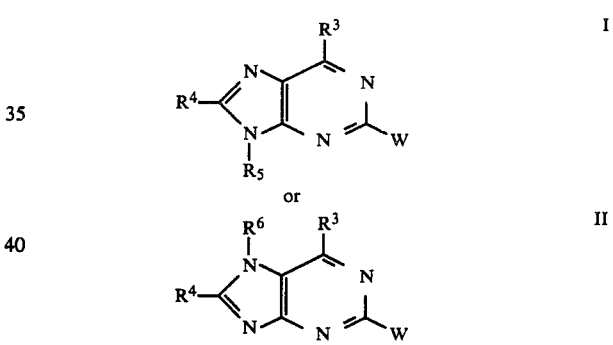

wherein: W is selected from the group consisting of —SRCONR$^1$R$^2$, —SRCN, and —SRCOR$^1$; in which R is selected from the group consisting of —(CH$_2$)$_n$—, where n is an integer from 1 to 5, and —(CH$_2$)$_n$—, wherein n is an integer from 1 to 5 having at least one side chain alkyl group containing from 1 to 5 carbon atoms; wherein R$^1$ and R$^2$ are the same or different, and selected from the group consisting of hydrogen, a straight chain alkyl group containing from 1 to 5 carbon atoms, and branched chain alkyl groups having from 1 to 5 carbon atoms; and wherein R$^3$, R$^4$, R$^5$ and R$^6$, are the same or different, and selected from the group consisting of a hydrogen, a straight chain alkyl group containing from 1 to 5 carbon atoms and a branched chain alkyl group containing from 1 to 5 carbon atoms; or a non-toxic salt thereof; in combination with a pharmaceutically acceptable adjuvant, carrier or diluent.

6. A pharmaceutical composition as defined in claim 5, further comprising an effective amount of an antibiotic selected from the group consisting of phleomycin, bleomycin, and mixtures thereof.

7. An amplifying pharmaceutical composition useful with antibiotics in the treatment of tumors and bacterial infections comprising an amplifying amount of a compound having the formula:

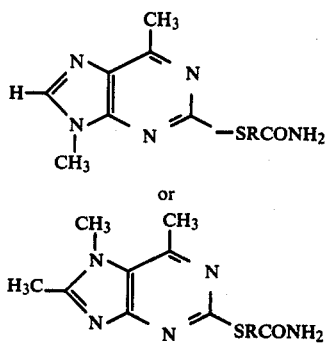

wherein R is selected from the group consisting of —$(CH_2)_n$—, wherein n is an integer from 1 to 5, and —$(CH_2)_n$—, wherein n is an integer from 1 to 5 having at least one side chain alkyl group containing from 1 to 5 carbon atoms; or a non-toxic salt thereof; in combination with a pharmaceutically acceptable adjuvant, carrier or diluent.

8. A pharmaceutical composition as defined in claim 7, further comprising an effective amount of an antibiotic from the group consisting of phleomycin, bleomycin and mixtures thereof.

9. An amplifying pharmaceutical composition useful with antibiotics in the treatment of tumors and bacterial infections which comprises an amplifying amount of at least one compound selected from the group consisting of 2-carbamoylmethylthio-6,9-dimethylpurine and 2-carbamoylmethylthio-6,8,9-trimethylpurine in combination with a pharmaceutically acceptable adjuvant, carrier or diluent.

10. A pharmaceutical composition as defined in claim 9, further comprising an effective amount of an antibiotic from the group consisting of phleomycin, bleomycin and mixtures thereof.

11. A method of treatment of tumors and bacterial infections which are normally responsive to the action of phleomycin, bleomycin, and mixtures thereof in an animal which comprises administering to the animal an effective amount of a compound selected from the group consisting of phleomycin, bleomycin, and mixtures thereof, prior to, simultaneous with or following administration of an amplifying amount of a compound of the formula:

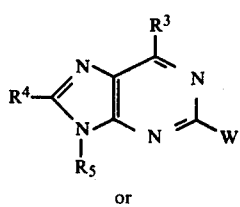

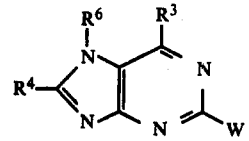

wherein: W is selected from the group consisting of —$SRCONR^1R^2$, —SCRN, and —$SRCOR^1$; in which R is selected from the group consisting of —$(CH_2)_n$—, where n is an integer from 1 to 5, and —$(CH_2)_n$—, wherein n is an integer from 1 to 5, having at least one side chain alkyl group containing from 1 to 5 carbon atoms; wherein $R^1$ and $R^2$ are the same or different, and selected from the group consisting of hydrogen, a straight chain alkyl group containing from 1 to 5 carbon atoms, and branched chain alkyl groups having from 1 to 5 carbon atoms; and wherein $R^3$, $R^4$, $R^5$ and $R^6$, are the same or different and selected from the group consisting of a hydrogen, a straight chain alkyl group containing from 1 to 5 carbon atoms and a brached chain alkyl group containing from 1 to 5 carbon atoms; or a non-toxic salt thereof.

12. A method for the treatment of tumors and bacterial infections which are normally responsive to the action of phleomycin, bleomycin and mixtures thereof in an animal which comprises administering to the animal an effective amount of a compound selected from the group consisting of phleomycin, bleomycin and mixtures thereof, prior to, simultaneous with or following administration of an amplifying amount of a compound having the formula:

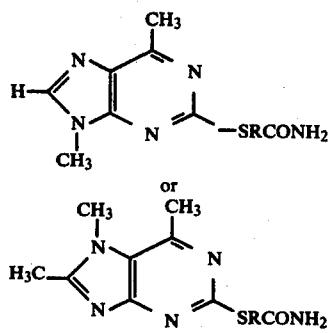

wherein R is selected from the group consisting of —$(CH_2)_n$—, wherein n is an integer from 1 to 5, and —$(CH_2)_n$—, wherein n is an integer from 1 to 5 having at least one side chain alkyl group containing from 1 to 5 carbon atoms; or a non-toxic salt thereof.

13. A method for the treatment of tumors and bacterial infections which are responsive to the action of phleomycin, bleomycin and mixtures thereof in an animal which comprises administering to the animal an effective amount of a compound selected from the group consisting of phleomycin, bleomycin and mixtures thereof prior to, simultaneous with, or following administration of an amplifying amount of at least one compound selected from the group consisting of 2-carbamoylmethylthio-6,9-dimethylpurine and 2-carbamoylmethylthio-6,8,9-trimethylpurine.

* * * * *